(12) United States Patent
Aguilar et al.

(10) Patent No.: US 8,916,177 B2
(45) Date of Patent: *Dec. 23, 2014

(54) METHOD FOR TREATING PREMATURE EJACULATION WITH A BOTULINUM NEUROTOXIN

(71) Applicant: Allergan, Inc., Irvine, CA (US)

(72) Inventors: Ivan Aguilar, Sinaloa (MX); Gustavo M. Gaxiola, Sinaloa (MX); Gilberto P. Paz, Jalisco (MX)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/081,993

(22) Filed: Nov. 15, 2013

(65) Prior Publication Data

US 2014/0140981 A1 May 22, 2014

Related U.S. Application Data

(63) Continuation of application No. 13/654,808, filed on Oct. 18, 2012, now Pat. No. 8,617,570, and a continuation of application No. 13/402,755, filed on Feb. 22, 2012, now Pat. No. 8,329,193, and a continuation of application No. 12/548,073, filed on Aug. 26, 2009, now Pat. No. 8,147,848.

(51) Int. Cl.
A61K 39/08 (2006.01)
A61K 38/48 (2006.01)

(52) U.S. Cl.
CPC .................................. *A61K 38/4893* (2013.01)
USPC ...................................................... 424/239.1

(58) Field of Classification Search
CPC .................... A61K 38/4893; C12Y 304/24069
See application file for complete search history.

(56) References Cited

U.S. PATENT DOCUMENTS

| 6,776,991 B2 | 8/2004 | Naumann |
| 7,105,516 B2 | 9/2006 | Denhart |
| 2006/0216313 A1 | 9/2006 | Brooks |

FOREIGN PATENT DOCUMENTS

WO 2009055351 A1 4/2009

OTHER PUBLICATIONS

Abdelhafeez I et al., The clinical response of obstructive benign prostatic enlargement (BPE) to botulinum toxin A (BTX-A) injection locally: A report on selected cases with 12 months follow-up. Neurourol Urodyn 2008;27(7):588-9 ABS-16—AN-2008123307.

Brisinda G et al., Athanassios Oeconomou, Helmut Madersbacher, Gustav Kiss, Thomas J. Berger, Michael Melekos and Peter Rehder. Is botulinum neurotoxin type A (BoNT-A) a novel therapy for lower urinary tract symptoms due to benign prostatic enlargement? A review of the literature + Author Reply, Eur Urol 2009;56(1):e10-e13 , AN-2009061241.

Bruskewitz R and MIST Study Group. Changes in sexual function in men randomized into a two-stage phase II trial of 100 and 300 units botulinum neurotoxin type A (BoNT-A) for the management of benign prostatic hyperplasia (BPH). J Urol 2009;181(4 Suppl):528 ABS-MA1477—AN-2009040970.

Chuang Yao-Chi et al., Botulinum toxin A improves refractory benign prostatic hyperplasia symptoms. J Urol Apr. 2004;171(Suppl 4):401 ABS 1524—AN-2004051046.

Chuang Y-C and Chancellor MB. In: Jankovic J, ed., Application of botulinum toxin in the prostate. Botulinum toxin: Therapeutic clinical practise & science Philadelphia, PA: Saunders Elsevier; 2009:pp. 273-282—AN-2009061102.

de Kort LM et al., Clinical, urodynamic and histologic results of intraprostatic injections with botulinum toxin type A for lower urinary tract symptoms due to benign prostatic hyperplasia. J Urol 2009;181(4 Suppl):703 ABS-MA1945—AN-2009040981.

Jones, High Performance, News and Views, Nature Aug. 3, 1989;340-348—91082334.

Lim SK et al., Intraprostatic and bladder-neck injection of botulinum A toxin in treatment of males with bladder-neck dyssynergia: A pilot study + Commentaries, Eur Urol 2008;53(3):620-7—AN-2007111760.

Mostachio GQ et al., Effect of boutulinum toxin A on seminal composition in male dogs with benign prostatic hyperplasia (BPH), Reprod Domest Anim 2008;43(Suppl 5):68 ABS P52—AN-200812349.

Oeconomou A et al., Editorial comment: Is botulinum neurotoxin type A (BoNT-A) a novel therapy for lower urinary tract symptoms due to benign prostatic enlargement? A review of the literature, J Urol 2008;182(1):235-236—AN-2009071458.

Parka SJ and Shin SM, Intraprostatic injection of botulinum toxin for men with Chronic pelvic pain syndrome, Eur Urol Suppl Apr. 2006;5(2):249 ABS-908—AN-2007010130.

Serefoglu EC and Silay, Botulinum toxin-A injection may be beneficial in the treatment of life-long premature ejaculation—MS. Med Hypotheses 2009;74(1):83-4—AN-2009092348.

Shaeer, et al., Botulinum Toxin A (Botox) for Relieving Penile Retraction, Original Research—Men's Sexual Health,—J Sex Med 2009;6:2788-2794, Abstract.

Shin SM and Park DS., Multi-regional injections of low dose botulinum toxin A for men with chronic pelvic pain syndrome, J Urol 2006;175(4 Suppl):34 ABS-104-AN-2007081365Shin SM and Park DS., Multi-regional injections of low dose botulinum toxin A for men with chronic pelvic pain syndrome, J Urol 2006;175(4 Suppl):34 ABS-104—AN-2007081365.

*Primary Examiner* — Brian J Gangle

(74) *Attorney, Agent, or Firm* — Brigitte C. Phan; Ted A. Chan; Debra Condino

(57) ABSTRACT

Methods for prolongation of climax time in a patient in need thereof are presented, as are methods for treating premature ejaculation by local administration of a Clostridial neurotoxin, such a botulinum neurotoxin, to the patient, are provided.

20 Claims, No Drawings

METHOD FOR TREATING PREMATURE EJACULATION WITH A BOTULINUM NEUROTOXIN

CROSS REFERENCE TO RELATED APPLICATIONS

This application is a continuation of U.S. application Ser. No. 13/654,808 which is a continuation of U.S. application Ser. No. 13/402,755, filed Feb. 22, 2012, now U.S. Pat. No. 8,329,193, which is a continuation of U.S. application Ser. No. 12/548,073, filed Aug. 26, 2009, now U.S. Pat. No. 8,147,848, all of which are incorporated by reference in their entirety.

BACKGROUND

Methods for treating premature ejaculation are presented. More particularly and in one aspect, methods for treating premature ejaculation by administration of a neurotoxin, such a botulinum neurotoxin, to a patient are provided.

Premature ejaculation (PE) is a common sexual dysfunction in men, particularly those in the age range of about 18 to about 40 years old. Premature ejaculation can be generally defined as the occurrence of ejaculation prior to or sooner than hoped for by one or both sexual partners [e.g. see 'The Merck Manual', 16$^{th}$ Edition, p 1576, published by Merck Research Laboratories, 1992]. As one example, premature ejaculation can be experienced as ejaculation before, upon or shortly after penile penetration of a sexual partner. If the instances of premature ejaculation are few and far between, then such occurrences may not be a cause for concern. However, if instances of premature ejaculation occur practically every time intercourse is attempted, or even if premature ejaculation occurs even greater than about 10% or about 20% of the time intercourse is attempted, then treatment of the condition is likely to be warranted.

Premature ejaculation may be classified as primary or secondary, in accordance with the Diagnostic and Statistical Manual of Mental Disorders, Fourth Edition (DSM-IV), which classifies sexual disorders into 4 particular categories: (1) primary, (2) general medical condition-related, (3) substance-induced, and (4) not otherwise specified. Primary applies to individuals who have had the condition since they became capable of functioning sexually (i.e., postpuberty). Secondary indicates that the condition manifests itself in an individual where an acceptable level of ejaculatory control was previously had, and then began to experiencing premature ejaculation thereafter. With secondary premature ejaculation, the problem does not relate to a general medical disorder, and it is usually not related to substance inducement, however, hyperexcitability might in particular instances relate to psychotropic drug use and resolves when the drug is withdrawn.

The prevalence rate of premature ejaculation in American males is estimated to range from 30-70%. The National Health and Social Life Survey (NHSLS) indicates a prevalence of 30%, which is fairly steady through all adult age categories. Premature ejaculation can occur at virtually any age in an adult man's life. As a reported condition, it is most common in younger men (aged 18-30 years old) but may also occur in conjunction with secondary impotence in men aged 45-65 years.

Compositions that can be utilized for treating premature ejaculation are known. For example, use of selective serotonin reuptake inhibitors (SSRI's) for treating premature ejaculation are known and claimed, for example, in U.S. Pat. No. 7,105,516 which is directed to novel SSRI's effective for the treatment of premature ejaculation, as well as U.S. Pat. No. 6,777,437. Additional methods for treating premature ejaculation can be found in U.S. Pat. No. 6,974,839, which teaches administration of an effective amount of a tramadol (a monoamine uptake inhibitor) material to a male prior to sexual intercourse, and in U.S. Pat. No. 6,495,154, which claims delaying the onset of ejaculation in a male by systemically administering to the individual a rapid-release pharmaceutical formulation containing clomipramine and pharmacologically acceptable acid addition salts thereof. U.S. Pat. No. 7,018,648 is directed to a transdermal device for administering testosterone and/or at least one derivative thereof to treat premature ejaculation; U.S. Pat. No. 6,593,335 is directed to method of treating premature ejaculation by administration of a potassium channel opener; U.S. Pat. No. 6,727,283 discloses oral ingestion of an essentially nonaqueous, liquid concentrate of sertraline hydrochloride. In some examples, fluoxetine or paroxetine, (20 mg and 40 mg, respectively, and taken daily) are also prescribed in order to treat premature ejaculation. Other approaches that are known include application of topical anesthetics, such as lidocaine 5% cream, for example, to the penis before intercourse. Drawbacks associated with the use such anesthetics include undesired reduction in sensitivity and/or short term inability of the patient to achieve an erection.

The anaerobic, gram positive bacterium *Clostridium botulinum* produces a potent polypeptide neurotoxin, botulinum neurotoxin, which causes a neuroparalytic illness in humans and animals referred to as botulism, however this neurotoxin has now been utilized for decades for treating various conditions in human beings. One unit (U) of botulinum toxin is defined as the $LD_{50}$ upon intraperitoneal injection into female Swiss Webster mice weighing 18-20 grams each. In other words, one unit of botulinum toxin is the amount of botulinum toxin that kills 50% of a group of female Swiss Webster mice. Seven generally immunologically distinct botulinum neurotoxins have been characterized, these being respectively botulinum neurotoxin serotypes A, B, $C_1$, D, E, F, and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. The botulinum toxins apparently bind with high affinity to cholinergic motor neurons, are translocated into the neuron and block the presynaptic release of acetylcholine.

Botulinum toxins have been used in clinical settings for the treatment of neuromuscular disorders characterized by hyperactive skeletal muscles. Botulinum toxin type A was approved by the U.S. Food and Drug Administration in 1989 for the treatment of essential blepharospasm, strabismus and hemifacial spasm in patients over the age of twelve. In 2000 the FDA approved commercial preparations of type A and type B botulinum toxin serotypes for the treatment of cervical dystonia, and in 2002 the FDA approved a type A botulinum toxin for the cosmetic treatment of certain hyperkinetic (glabellar) facial wrinkles. Clinical effects of peripheral intramuscular botulinum toxin type A are usually seen within one week of injection and sometimes within a few hours. The typical duration of flaccid muscle paralysis from a single intramuscular injection of botulinum toxin type A can be about three months, although in some cases the effects of a botulinum toxin induced denervation of a gland, such as a salivary gland, have been reported to last for several years.

Although all the botulinum toxins serotypes apparently inhibit release of the neurotransmitter acetylcholine at the neuromuscular junction, they do so by affecting different neurosecretory proteins and/or cleaving these proteins at different sites. Botulinum toxin A is a zinc endopeptidase which can specifically hydrolyze a peptide linkage of the intracellular, vesicle associated protein SNAP-25. Botulinum type E also cleaves the 25 kiloDalton (kD) synaptosomal associated protein (SNAP-25), but targets different amino acid sequences within this protein, as compared to botulinum toxin type A. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (H chain) and a cell surface receptor; the receptor is thought to be different for each serotype of botulinum toxin and for tetanus toxin. The carboxyl end segment of the H chain, $H_c$, appears to be important for targeting of the toxin to the cell surface. In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol. The last step of the mechanism of botulinum toxin activity appears to involve reduction of the disulfide bond joining the H and L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kDa. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kDa, 500 kDa and 300 kDa forms. Botulinum toxin types B and $C_1$ are apparently produced as only a 500 kDa complex. Botulinum toxin type D is produced as both 300 kDa and 500 kDa complexes. Finally, botulinum toxin types E and F are produced as only approximately 300 kDa complexes. The complexes (i.e. molecular weight greater than about 150 kDa) are believed to contain a non-toxin hemagglutinin protein and a non-toxin and non-toxic nonhemagglutinin protein. These two non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kDa molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. The toxin protein has a marked instability upon removal of the hemagglutinin protein.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for a lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, Properties and use of Botulinum toxin and Other Microbial Neurotoxins in Medicine, Microbiol Rev. 56: 80-99 (1992). Generally, the botulinum toxin type A complex can be isolated and purified from an anaerobic fermentation by cultivating *Clostridium botulinum* type A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kDa crystalline botulinum toxin type A complex with a specific potency of $3 \times 10^7$ $LD_{50}$ U/mg or greater. This known process can also be used, upon separation out of the non-toxin proteins, to obtain pure botulinum toxins, such as for example: purified botulinum toxin type A with an approximately 150 kDa molecular weight with a specific potency of $1\text{-}2 \times 10^8$ $LD_{50}$ U/mg or greater; purified botulinum toxin type B with an approximately 156 kDa molecular weight with a specific potency of $1\text{-}2 \times 10^8$ $LD_{50}$ U/mg or greater, and; purified botulinum toxin type F with an approximately 155 kDa molecular weight with a specific potency of $1\text{-}2 \times 10^7$ $LD_{50}$ U/mg or greater.

Already prepared and purified botulinum toxins and toxin complexes suitable for preparing pharmaceutical formulations can be obtained from List Biological Laboratories, Inc., Campbell, Calif.; the Centre for Applied Microbiology and Research, Porton Down, U.K.; Wako (Osaka, Japan), as well as from Sigma Chemicals of St Louis, Mo.

It has been reported that a botulinum toxin has been used in clinical settings as follows:
(1) about 75-125 units of BOTOX® per intramuscular injection (multiple muscles) to treat cervical dystonia;
(2) 5-10 units of BOTOX® per intramuscular injection to treat glabellar lines (brow furrows) (5 units injected intramuscularly into the procerus muscle and 10 units injected intramuscularly into each corrugator supercilii muscle);
(3) about 30-80 units of BOTOX® to treat constipation by intrasphincter injection of the puborectalis muscle;
(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
  (a) flexor digitorum profundus: 7.5 U to 30 U
  (b) flexor digitorum sublimis: 7.5 U to 30 U
  (c) flexor carpi ulnaris: 10 U to 40 U
  (d) flexor carpi radialis: 15 U to 60 U
  (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.
(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Jyons, J., et al., Tremor-Predominant Parkinson's Disease, Drugs & Aging 16(4); 273-278:2000.

Treatment of certain gastrointestinal and smooth muscle disorders with a botulinum toxin are known. See e.g. U.S. Pat. Nos. 5,427,291 and 5,674,205 (Pasricha). Additionally, transurethral injection of a botulinum toxin into a bladder sphincter to treat a urination disorder is known (see e.g. Dykstra, D. D., et al, Treatment of detrusor-sphincter dyssynergia with botulinum A toxin: A double-blind study, Arch Phys Med Rehabil 1990 January; 71:24-6), as is injection of a botulinum toxin into the prostate to treat prostatic hyperplasia. See e.g. U.S. Pat. No. 6,365,164 (Schmidt).

U.S. Pat. No. 5,766,605 (Sanders) proposes the treatment of various autonomic disorders, such as hypersalivation and rhinitis, with a botulinum toxin.

Furthermore, various afflictions, such as hyperhidrosis and headache, treatable with a botulinum toxin are discussed in WO 95/17904 (PCT/US94/14717) (Aoki). EP 0 605 501 B1 (Graham) discusses treatment of cerebral palsy with a botulinum toxin and U.S. Pat. No. 6,063,768 (First) discusses treatment of neurogenic inflammation with a botulinum toxin. Erectile dysfunction has been reported as a symptom of botulism. Jenzer G., et al., Autonomic dysfunction in botulism B: a clinical report, Neurology 1975; 25:150-153; Naumann M. et al., Pure autonomic dysfunction in botulism type B, Naunyn Schmiedeberg's Archives of Pharmacology June 2002 (supp 2); 365 (abstract 89 at R31). This may be a result of circulating botulinum toxin present in a patient with botulism acting to block release of acetylcholine from cholinergic parasympathetic nerve endings in the corpora cavernosa of the penis. This would cause an inhibition of penile smooth muscle relaxation and therefore a reduced flow of blood into penile structures, and hence a flaccid penis. Contrarily, it has been speculated that a botulinum toxin can be used to cause an erection of the penis. Jones D. High performance. Nature 1989; 3:348.

It is known that botulinum toxin type A can have an efficacy for up to 12 months (European J Neurology 6 (Supp 4): S111-S1150:1999), and in some circumstances for as long as 27 months. The Laryngoscope 109:1344-1346:1999. However, the usual duration of an intramuscular injection of BOTOX® is typically about 3 to 4 months. The success of botulinum toxin type A to treat a variety of clinical conditions has led to interest in other botulinum toxin serotypes. Additionally, pure botulinum toxin has been used to treat humans. see e.g. Kohl A., et al., Comparison of the effect of botulinum toxin A BOTOX® with the highly-purified neurotoxin (NT 201) in the extensor digitorum brevis muscle test, Mov Disord 2000; 15(Suppl 3): 165. Hence, a pharmaceutical composition can be prepared using a pure botulinum toxin.

The botulinum toxin molecule (about 150 kDa), as well as the botulinum toxin complexes (about 300-900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection. A commercially available botulinum toxin containing pharmaceutical composition is sold under the trademark BOTOX® (available from Allergan, Inc., of Irvine, Calif.). BOTOX® consists of a purified botulinum toxin type A complex, albumin, and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A complex, 0.5 milligrams of human serum albumin and 0.9 milligrams of sodium chloride in a sterile, vacuum-dried form without a preservative.

To reconstitute vacuum-dried BOTOX® sterile normal saline without a preservative; 0.9% Sodium Chloride injection is used by drawing up the proper amount of diluent in the appropriate size syringe. Since BOTOX® is denatured by bubbling or similar violent agitation, the diluent is gently injected into the vial. BOTOX® should be administered within four hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer at or below −5° C. BOTOX® is administered within four hours after the vial is removed from the freezer and reconstituted. During these four hours, reconstituted BOTOX® can be stored in a refrigerator (2° to 8° C.).

Other commercially available botulinum toxin containing pharmaceutical compositions include DYSPORT® (*Clostridium botulinum* type A toxin haemagglutinin complex with albumin and lactose in the formulation, available from Ipsen Limited, Berkshire, U.K. as a powder to be reconstituted with 0.9% sodium chloride before use), and MYOBLOC™ (an injectable solution comprising botulinum toxin type B, human serum albumin, sodium succinate, and sodium chloride at about pH 5.6, available from Solstice Neurosciences, Inc).

What is needed therefore is a simple method for treating premature ejaculation and/or prolongation of climax time. In particular, a long lasting, non-systemic method for treating premature ejaculation and/or prolongation of climax time is desired that does not entail oral or repeated ingestion of a pharmaceutical compound prior to engaging in sexual activity.

SUMMARY

The present invention meets this need and provides an effective and long lasting method for treatment for premature ejaculation and/or prolongation of climax time in a patient in need thereof. In one example a method for treating premature ejaculation in a patient in need thereof is provided, the method comprising the step of locally administering a Clostridial neurotoxin to the patient to thereby treat premature ejaculation of the patient. As an example, local administration of a therapeutic amount of Clostridial neurotoxin, in accordance with the methods herein disclosed, is accomplished by transdermal, intramuscular, subcutaneous, subdermal, intradermal or implant administration. In one embodiment, local administration of a therapeutic amount of Clostridial neurotoxin is by injection into the patient, such as into the penis, for example. A preferable Clostridial neurotoxin for use in the methods herein described is a botulinum neurotoxin, which can be selected from the group consisting of botulinum neurotoxin types A, B, C, D, E, F and G, and is preferably botulinum neurotoxin type A. Various ranges/amount of botulinum neurotoxin can be therapeutically administered in accordance with the teachings of the present disclosure, for example, botulinum toxin can be administered in an amount of from about 1 unit to 20,000 units, dependent, of course, on the potency of the botulinum toxin type utilized and its method of administration (e.g. an amount of botulinum toxin contained in a slow-release implant or pulsatile implant can be many times greater than an amount of botulinum toxin that is administered directly and at once, rather than slowly released from an implant). Exemplary useful amounts for a botulinum neurotoxin type A or type B, can be from about 1 unit to 2500 units or from about 100 to about 15,000 units, respectively, or an amount or range therebetween.

In a particular embodiment, local administration of the therapeutic amount of the Clostridial neurotoxin to the patient is accomplished via injection of the Clostridial neurotoxin into one or more locations of a penis of the patient.

DEFINITIONS

As used herein, the words or terms set forth below have the following definitions. "About" means approximately or nearly and in the context of a numerical value or range set forth herein means±10% of the numerical value or range recited or claimed. "Therapeutically effective amount," as used herein, means an amount of a Clostridial neurotoxin, for example a botulinum toxin type A, B, C, D, E, F and G, that ameliorates, or eliminates one or more symptoms of a particular disease or condition or prevents or delays the onset of one or more symptoms of a particular disease or condition. "Local administration" means direct administration by a non-systemic route at or in the vicinity of the site of an affliction or disorder. Thus, local administration of a pharmaceutical comprising a Clostridial neurotoxin, such as a botulinum neurotoxin, excludes intravenous or oral administration, but includes, for example, intramuscular, transdermal or subcutaneous injection or placement of an implant for administration of the neurotoxin.

"Treating" means to alleviate (or to eliminate) at least one symptom, either temporarily or permanently. Here, this includes increasing the time (i.e. prolongation of climax time) it takes a patient to reach climax after sexual arousal. In a particular example, climax time is the time between the start of intercourse and the time at which climax is achieved. The Clostridial toxin is preferably a botulinum toxin (as either a complex or as a pure toxin [i.e. about 150 kDa molecule, the neurotoxic component of botulinum toxin, free of complexing proteins], such as a botulinum toxin A, B, C, D, E, F or G. Administration of the Clostridial toxin can be via a transdermal route (e.g. by application of a Clostridial toxin in a cream, patch or lotion vehicle), subdermal route (i.e. subcutaneous or intramuscular injection) or by an intradermal route of administration.

"Neurotoxin" includes Clostridial neurotoxins both as pure toxin and complexed with one to more non-toxin, toxin associated proteins, whether made by the native Clostridial bacterium or by recombinant means in a non-Clostridial species. "Botulinum neurotoxin" means non-complexed botulinum neurotoxin (i.e. pure botulinum neurotoxin molecule having a molecular weight of about 150 kDa) or as a complex (i.e. having a molecular weight of about 300 to about 900 kDa weight complex comprising a neurotoxin molecule and one or more associated non-toxic molecules), and excludes botulinum toxins which are not neurotoxins such as the cytotoxic botulinum toxins $C_2$ and $C_3$, but can include recombinantly made, hybrid, modified, and chimeric botulinum toxins.

"Patient" means a human subject receiving medical care.

"Climax baseline time" is the pre-treatment climax time of a patient, that is, the time or average time that it takes for a patient to climax after becoming sexually aroused.

"Prolongation of climax time" means an increase in time (increase in climax baseline time) from which a patient becomes sexually aroused to the time of sexual climax (i.e. orgasm). In one aspect, "treating premature ejaculation" means increasing the time between the beginning of sexual arousal of a patient and ejaculation by the patient; and in particular instances, it can mean increasing the time from which sexual intercourse begins to the time of ejaculation.

The present invention encompasses a method for treating premature ejaculation by local administration of a Clostridial toxin to a mammal, such as a human patient. Preferably, the botulinum toxin is a botulinum toxin type A. The botulinum toxin can be administered in an amount between about 1 unit and about 10,000 units and premature ejaculation and/or prolongation of climax time can be alleviated for between about 2 weeks and about 6 months. In particular examples, premature ejaculation and/or prolongation of climax time can be alleviated from about 2 months to about 6 months, or from about 4 to about 6 months, for example. In one aspect, the local administration step is carried out by direct administration of the Clostridial toxin, such as a botulinum neurotoxin, to at least one location of a penis of the patient.

In another embodiment, a method for treating premature ejaculation in a patient in need thereof is provided, where the method comprises a step of locally administering, by injection, a botulinum neurotoxin to a penis of the patient, thereby treating premature ejaculation in the patient. In particular embodiments, the botulinum neurotoxin is injected into at least two penile locations, and in some examples at least three penile locations. In specific examples, local administration of botulinum neurotoxin is to a frenulum of the penis, exemplary amounts being from 1 to about 2500 units of a botulinum toxin type A. When utilizing a botulinum toxin type B for example, the administered amount can be from between about 1 unit and about 25,000 units, or from about 100 units to about 20,000 units or from about 500 units to about 15,000 units or any amount therebetween.

As another example, a method for treating premature ejaculation in a patient in need thereof is herein provided where botulinum neurotoxin type A is locally administered to at least one location of a penis of the patient, wherein the location is the frenulum and/or glans of the penis, to thereby treating premature ejaculation in the patient, wherein exemplary useful amounts include administering to at least the one location from about 1 unit to about 2500 units of botulinum neurotoxin. In particular embodiments, additional administration of botulinum neurotoxin to the penis of the patient can be performed, for example from about least about 2 months to about 3 months or more after an initial administration of botulinum neurotoxin to the penis. In particular embodiments, local administration of the botulinum neurotoxin type A is from about 1 unit to about 500 units, per injection site, per patient visit. Exemplary botulinum neurotoxin administration can be to a single location on the penis (e.g. frenulum) or distributed over two or more anatomically distinct portions of the penis (e.g. penile frenulum, penile prepuce/foreskin, glans penis, urethral opening).

Additionally, a method for prolongation of climax time in a patient in need thereof is provided wherein the method comprises the step of locally administering a botulinum neurotoxin to the patient to thereby prolong the climax time in the patient. Administration of botulinum neurotoxin can be via transdermal, intramuscular, subcutaneous, subdermal, intradermal or implant administration, and can be to a frenulum or prepuce, for example. In particular embodiments, the botulinum neurotoxin is administered by injection and the botulinum neurotoxin is botulinum neurotoxin type A or type B.

The age range of patients upon which the methods herein disclosed can be practiced can be from about 18 year old to about 60 years old, more particularly, from about 18 years old to about 40 years old, and even more particularly, from about 18 years old to about 30 years old. In particular instances, the patient has tried various previous treatments that have not been found to satisfactorily treat the patient's premature ejaculation.

Patients that can be treated by the methods herein disclosed may have previously partaken in regimens for treating their premature ejaculation or for prolongation of their climax time. Exemplary regiments can include taking a selective serotonin reuptake inhibitor, such as fluoxetine or paroxetine, for example. Other approaches that may have been tried include application of topical anesthetics, such as lidocaine 5% cream, applied to the penis before intercourse. Such approaches can, if desired, be combined with the methods herein disclosed in order to treat premature ejaculation or for prolongation of climax time.

In particular embodiments the botulinum neurotoxin is administered on an as-needed basis. Dosing will be determined for, and be particular to, the patient/particular presentation of premature ejaculation, with non-limiting, exemplary amounts provided herein. Duration of effect after botulinum administration can be up to about 4 months after administration, for example. In particular instances, the duration of effect after botulinum administration can be from about 2 days to about 3 months after botulinum administration. Shorter duration of effects can be associated with a botulinum toxin having a short acting profile/duration of effect, such as botulinum toxin type E, relative to another botulinum toxin, such as a botulinum toxin type A, for example.

Description

Methods for treating premature ejaculation are herein provided, by locally administering a Clostridial toxin, preferably a botulinum toxin selected from the group consisting of botulinum toxin type A, B, C, D, E, F and G, more preferably botulinum toxin type A or B, most preferably botulinum toxin type A, to a patient in need thereof. Methods herein disclosed provide patients the ability to prolong climax time and/or treat premature ejaculation via a safe, easy, long lasting treatment method that can have a duration of desired effect for up to about 6 months.

There are several useful ways by which the Clostridial toxin may be locally administered. For example, transdermal methods for administering a botulinum toxin are known in the art, utilizing various botulinum formulations. Such formulations can be water-based, as currently available commercial forms of botulinum toxin are diluted with, or supplied in, saline. However, other aqueous or non-aqueous delivery carriers, such as creams, lotions, gels, ointments, or emulsions are also contemplated (for transdermal administration of botulinum toxins see, for example the following non-exhaustive list: U.S. patent application No. 20040009180, filed Jul. 11, 2002 entitled "Transdermal botulinum toxin compositions"; U.S. patent application No. 20090087457, filed Mar. 3, 2006 entitled "Compositions and Methods for Topical Application and Transdermal Delivery of Botulinum Toxins"; U.S. patent application No. 20070116724 filed Nov. 16, 2006 entitled "Compositions and Methods of Topical Application and Transdermal Delivery of Botulinum Toxins without Reduced Non-Toxin Proteins"; U.S. patent application No. 20030113349, filed Dec. 18, 2002 entitled "Topically applied *clostridium botulinum* toxin compositions and treatment methods"; U.S. patent application No. 20080220021, filed May 23, 2008 entitled "Topical Botulinum Toxin Compositions for the Treatment of Hyperhidrosis"; WIPO Publication No. WO/2008/070538, filed Nov. 30, 2007 entitled "Micellar Nanoparticles Comprising Botulinum Toxin" and U.S. Pat. No. 7,445,783 entitled "Topical and transdermal treatments using urea formulations", all such patents and patent applications are herein incorporated by reference in their entirety.

The present invention includes within its scope: (a) a botulinum neurotoxin complex as well as a pure botulinum neurotoxin obtained or processed by bacterial culturing, toxin extraction, concentration, preservation, freeze drying and/or reconstitution and; (b) modified or recombinant botulinum neurotoxin, that is botulinum neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of botulinum neurotoxins so made, and includes botulinum neurotoxins with one or more attached non-native targeting moieties for a cell surface receptor present on a cell.

Preferably, because of its clinical history to successfully treat a number of indications, a method within the scope of the present invention includes local administration of a botulinum type A or botulinum toxin type B, although botulinum toxin type B is used with a larger protein load, as compared to type A toxin. A botulinum toxin type A used in a method within the scope of the present invention can be a complex of toxin and non-toxin proteins, which together comprise a total molecular weight of up to about 900 kDa. Dosage ranges and amounts, like any pharmaceutical, are based upon size, age and health of the patient, as well as upon the particular commercial preparation of the botulinum toxin used. As known in the art, therapeutic use of botulinum toxins is tailored to the particular patient that is presented for treatment, e.g. to treat premature ejaculation. A botulinum toxin type B used in a method within the scope of the present invention can be a pure toxin or complex of toxin and non-toxin proteins, which is used at a dose of between about 50 and about 20,000 units. Other botulinum toxin serotypes may be used in proportion to the dosages and concentrations exemplified herein, according to their respective levels of biological activity. For example, most units listed in the instant disclosure are of BOTOX®, but different serotypes or strains of a botulinum toxin may be used, and different amounts may be administered. For example, about 3-4 times of DYSPORT® (a botulinum toxin type A complex available from Ipsen Inc.) than an amount of BOTOX® may be utilized; about 40-50 times of NEUROBLOC®/MYOBLOC® (a botulinum toxin type B available from Solstice Neurosciences) than an amount of BOTOX® may be utilized; and about equivalent amounts, in units, of XEOMIN® (pure botulinum toxin type A, by Merz Pharma) relative to BOTOX® units can be utilized, to achieve a desired therapeutic effect, respectively. The present invention also encompasses methods for concurrent or serial administration of a mixture of two or more of the above neurotoxins to effectively treat a patient with premature ejaculation.

In addition to transdermal methods for administering a botulinum toxin, injection of a botulinum toxin can be utilized to treat premature ejaculation and/or for prolongation of climax time. When injections are utilized, an appropriate needle for botulinum toxin injection can be utilized, such as, but are not limited to needles of 30-guage or smaller, preferably from about 23-gauge to about 25-gauge, and the area is preferably cleaned, such as with alcohol, before injection. Local anesthetic cream, general anesthesia, sedation or any known be useful anesthetic may be utilized, and may be necessary, depending upon the particular patient (some patients being more sensitive than others) undergoing treatment in accordance with the present methods. In particular examples, topical use of an anesthetic cream, such as, for example benzocaine, butamben, dibucaine, lidocaine, oxybuprocaine, pramoxine, proparacaine, proxymetacaine, and tetracaine can be applied before administration of the botulinum toxin via a needle. Additionally, needleless administration methods for delivery of botulinum toxins are well known in the art (see for example, U.S. Pat. Nos. 7,479,281 and 7,479,134 both herein incorporated by reference), and such administration/apparatus can be utilized as a delivery means for administration of botulinum toxin in accordance with the treatment methods herein disclosed.

In particular examples, topical lidocaine anesthetic cream is utilized and applied to the area to be injected. Other anesthetic methods can be utilized, such as blockade of the penile branches of the pudendal nerve, utilizing, for example, a 2% lidocaine injection (from about 5 cc to about 10 cc total of a 2% lidocaine preparation) administered to the base of the penis (to the anterior (ventral) and posterior (dorsal) of the base of the penis); and/or sometimes cooling of the area to be injected may be utilized, such as by the application of ice or cold air (cold air can be applied utilizing a "Zimmer Cryo 5" apparatus from Zimmer Medizin Systems, Irvine, Calif., for example).

The amount of the neurotoxin, such as a botulinum toxin, administered can vary widely according to the particular patient/case being treated, its severity and other various patient variables including size, weight, age, and patient responsiveness to therapy. Generally, the dose of botulinum neurotoxin to be administered will vary with the age, size and presenting condition of the patient to be treated. When therapeutically utilizing botulinum toxins, the potency of the neurotoxin to be administered is also a consideration (tailoring a particular dosage of botulinum toxin to a particular patient/case is well known in the botulinum neurotoxin arts).

In some instances, the dosage of botulinum neurotoxin administered can be increased until achieving the desired effect (e.g. until the patient is satisfied with the resultant delay in ejaculation). In a particular embodiment, a first dosage can be from about 10 units to about 75 units of a botulinum toxin, or from about 25 units to about 50 units of a botulinum toxin, such as BOTOX®. If unsatisfactory results are observed, treatment dosage can be increased, as determined by the medical practitioner's evaluation of the particular case at hand, the dosage, for example, being increased up to about 100 units of a botulinum toxin. In such instances, the time between administration of increasing dosages of botulinum toxin can be about 3 weeks, preferably about 1 month and most preferably about 2 months.

The present methods for treating premature ejaculation and/or prolongation climax time can be practiced, for example, on patient of about 18 years old to about 60 years old, more particularly, from about 18 years old to about 40 years old, and even more particularly, from about 18 years old to about 30 years old. In any such patient, the problem of premature ejaculation can present itself as when the patient is not being able to abstain from ejaculation for a sufficient time as desired. For example, a patient may experience a "climax base time", that is, the time or average time that it takes for the patient to climax after becoming sexually aroused, of from about 1 minute to about 10 minutes. In particular instances, this may not even allow the patient to begin/achieve sexual intercourse if the patient prematurely ejaculates before even beginning sexual intercourse (e.g. before penile penetration of partner), or results in ejaculation instantly upon penile penetration or even attempting penetration. Clearly a patient that suffers from such a predicament would be well served by the treatment methods herein disclosed.

In some instances premature ejaculation can be experienced even after the beginning of sexual intercourse, that this, even if a patient is able to penetrate their partner (i.e. not ejaculate prior to penetration), ejaculation prematurely follows. In such instances, it is the time period between penetration and ejaculation that considered to be too short, and accordingly prolongation of climax time, here increasing the time from which sexual intercourse begins to the time of ejaculation, is desired. In particular non-limiting examples, a patient may be considered to suffer from premature ejaculation if ejaculation is achieved after from about 10 seconds to about 15 minutes after penetration, from about 15 seconds to about 10 minutes after penetration or from about 30 seconds to about 5 minutes after penetration. In particular cases, a patient may be considered to suffer from premature ejaculation if ejaculation is achieved after from about 10 seconds to about 3 minutes after penetration, from about 25 seconds to about 2 minutes after penetration or from about 30 seconds to about 1 minute after penetration.

Patients suffering from premature ejaculation may have found that previous treatment methods, such as ingestion of SSRIs (e.g. fluoxetine or paroxetine, 20 mg and 40 mg respectively and taken daily) did not sufficiently treat their premature ejaculation and thus will find the instant treatment methods to be useful, either in place of their selective serotonin reuptake inhibitor regimen or in conjunction with such a regimen. Previously undertaken approaches which may not have provided satisfactory results can also include use of topical anesthetic therapy, such as the application of a 5% lidocaine cream to a penis for example, prior to (e.g. about 10 minutes before) intercourse. The patient utilizing topical anesthetic therapy may find the instant treatment methods to be useful either in place of their topical anesthetic therapy regimen or in conjunction with a topical anesthetic therapy regimen.

Exemplary locations at which a botulinum toxin, such as botulinum toxin type A or B, may be administered include the penis. In particular, areas such as the glans, balanopreputial surface, frenulum, alone or in any combination for example, can be targeted for administration of a botulinum neurotoxin in order to treat premature ejaculation.

In exemplary embodiments, the area that is to receive the botulinum neurotoxin is cleaned utilizing alcohol, such as by utilizing an alcohol wipe, for example. If desired, local anesthetic (as disclosed herein) is then applied to the cleaned area, after which the botulinum neurotoxin is administered. Post-procedurally, the patient is instructed not to engage in sexual activity for the following 48 hours, and if edema and/or inflammation is observed, a cold compress or ice pack may be applied. Typically, patients observe effects (e.g. delaying of previously premature ejaculation) within about 48 to about 72 hours, with full results (maximum delay) usually observed after about 3 weeks. The following are non-limiting examples where patient's suffering from premature ejaculation are treated.

EXAMPLES

Example 1

Treatment of Premature Ejaculation

A 24 year old male presents at his doctor's office complaining that he climaxes within about 2 minutes after penetration of his partner (for this patient, his climax baseline time is 2 minutes). This is a subject of great consternation to the patient as well as his partner. The doctor treats the patient by cleaning the area to be injected with isopropyl alcohol and administering about 50 units of a botulinum toxin type A (BOTOX®) to the patient's penis, using a 30-gauge needle. Injection is into the glans of the penis and about 1 cm from the urethral opening and the patient is instructed to not have sex for 48 hours. At a follow-up visit, the patient reports experiencing a slight pain at the site of injection that disappeared within 24 hours of the injection, but otherwise no erectile dysfunction or loss of sensitivity is noted. The patient reports that he has doubled his climax baseline time (from about 2 to about 4 minutes), and frequently is even able to enjoy intercourse for longer than 4 minutes (greater than doubling his climax baseline time). These results, that is, prolonging the time this patient ejaculates after the start of intercourse, are observed for about 4 months after initial botulinum neurotoxin administration, after which the patient returns for re-injection of the same amount of botulinum toxin at the same location.

It is noted that in this instance, the doctor may have chosen to administer another botulinum preparation/serotype, if he so chooses, such as, for example, about 200 units of DYSPORT or about 50 units of XEOMIN (botulinum toxin type A preparations) or about 2500 units of MYOBLOC (botulinum toxin type B preparation).

Example 2

Treatment of Premature Ejaculation

A 32 year old male presents at his doctor's office complaining that every instance he engages in sexual intercourse, he climaxes within about 10 seconds after penetration of his partner (his climax baseline time is about 10 seconds), a situation that both the patient and his partner are growing quite tired of. Accordingly and after taking a detailed sexual history of the patient, the doctor determines that the patient is suffering from premature ejaculation and decides to administer botulinum neurotoxin to the patient. Accordingly, the doctor cleans the patient's penile frenulum over the anterior region of the glans with isopropyl alcohol and subsequently applies topical lidocaine anesthesia cream to anesthetize the area, after which 25 units of a botulinum neurotoxin (BOTOX®) is injected, utilizing a 25 gauge needle. Post procedure, the patient is instructed not to have sex during the following 48 hours. If edema and/or inflammation is noted, appropriate application of an ice-pack to the area is recommended (applied not longer than about 15 minutes at a time).

At a follow up session 2 weeks later, the patient reports that he is still unable to withhold ejaculation for greater than about 10 seconds. Accordingly, the doctor prepares the patient as before for the injection, this time administering 50 units of a botulinum neurotoxin (BOTOX®) and sends the patient along with the same post-procedure instructions. At a follow up session 3 weeks later, the patient reports a doubling in his climax baseline time, with on some occasions lasting for about 10 to 15 minutes, and that both he and his partner are very satisfied with the resultant outcome of the treatment.

Example 3

Treatment of Primary Premature Ejaculation

After suffering for decades, a 42 year old male visits his doctors office to report that his suffering from premature ejaculation precludes his ability to have sexual intercourse, since once sexually aroused, he prematurely ejaculates before even commencing with intercourse. He informs the doctor that he has been this way ever since reaching sexual maturity.

His physician decides to prescribe fluoxetine 20 mg, taken daily to see if this will help mitigate his primary premature ejaculation. After 2 months of taking the fluoxetine, the patient reports no change in his premature ejaculation before commencing intercourse. In addition to the daily fluoxetine, topical therapy is prescribed, in particular the patient is instructed to topically apply a 5% lidocaine cream about 10 minutes before intercourse. Three weeks later, the patient still reports no change in his situation.

The physician decides to administer a botulinum neurotoxin to the patient's penis. Accordingly, the area of the posterior region of the glans in the balanopreputial surface and the frenulum is cleaned with alcohol and a pudendal nervous blockade is applied, utilizing a 2% lidocaine injection to the dorsal and ventral portion of the penis base (the blockade administration of anesthetic being as utilized/similar to administration for a male circumcision, for example). About 50 units of botulinum toxin type A (BOTOX®) is injected into the posterior region of the glans in the balanopreputial area and another 25 units is administered to the frenulum. Post procedure, the patient is instructed not to have sex during the following 48 hours. If edema and/or inflammation is noted, appropriate application of an ice-pack to the area is recommended (not longer than about 15 minutes at a time), and the patient is instructed to continue with the fluoxetine. The patient reports back 2 weeks later that he is now able to penetrate and have intercourse with his partner for up to about 15 minutes without prematurely ejaculating, and these positive result are observed for about 3 months.

Example 4

Treatment of Secondary Premature Ejaculation

A 52 year old man presents at his doctor's office complaining that he is suffering from premature ejaculation. The patient informs the doctor that he previously has not suffered from this condition, however ever since he has become sexually involved with his latest partner, he has not been able to avoid episodes of premature ejaculation. The doctor decides to treat the patient by administering 2500 units of botulinum toxin type B (MYOBLOC™) to the frenulum of the patient. After injection, the patient is instructed not to have sex during the following 48 hours. The patient reports back 2.5 weeks later that he is now able to penetrate and have intercourse with his partner for up to about 15 minutes without prematurely ejaculating, and these positive result are observed for about 4 months, after which the patient returns for further botulinum toxin administration. This time, the doctor administers the botulinum toxin to the patient's frenulum utilizing a transdermal formulation of botulinum toxin type B. Positive results, with the patient able to withstand intercourse for a minimum of about 9 minutes before ejaculation occurs, is reported.

Treatments according to the methods disclosed herein have many advantages, including:
1. effective relief of premature ejaculation, typically including at least a doubling of a patient's climax baseline time, by utilizing a relatively quick onset of effect, typically first noted from about 48 to about 72 hours after administration of botulinum neurotoxin;
2. long term relief of premature ejaculation can be achieved, with observed duration of effect being from about 3 months to about 6 months after administration of botulinum neurotoxin;
3. there are no or minimal side effects from the practice of the disclosed invention, and the methods are localized and do not entail the ingestion and systemic circulation of pharmaceuticals that heretofore have been utilized in treating premature ejaculation;
4. use of the neurotoxins in accordance with the methods herein disclosed results in no erectile dysfunction or loss of sensitivity, unlike previously utilized methods for treating premature ejaculation.

Although the present invention has been described in detail with regard to certain preferred methods, other embodiments, versions, and modifications within the scope of the present invention are possible. For example, besides a botulinum toxin, other neurotoxins which can accomplish the same desired result (treatment of premature ejaculation by local administration of the toxin) are within the scope of the invention. Thus, a tetanus toxin can show efficacy as well as recombinant, chimeric and modified Clostridial toxins, including recombinant, chimeric and modified botulinum toxins. Additionally, the present invention includes a treatment of premature ejaculation by local administration of two or more neurotoxins, such as two or more botulinum toxins, are administered concurrently or consecutively. For example, botulinum toxin type A can be administered until a loss of clinical response or neutralizing antibodies develop, followed by administration of botulinum toxin type B or E. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect. Finally, use of a relatively short acting botulinum toxin, such as a botulinum toxin type E, where use of a short acting toxin is indicated, can also be utilized as herein disclosed to treat premature ejaculation, for example.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Variations of exemplary embodiments will become apparent to those of ordinary skill in the art upon reading the foregoing description. The inventors expects skilled artisans to employ such variations as appropriate, and the inventors intend for the invention to be practiced otherwise than specifically described herein. For example, particular doses and injection particulars such as number of administration sites and locations of administration to the patient, useful in accordance with the teachings of the present disclosure, are considered to be within the scope of the present invention. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations/methods of the present invention may be utilized in accordance with the teachings herein. Accordingly, the present invention is not limited to that precisely as shown and described.

We claim:

1. A method for treating premature ejaculation in a patient in need thereof, the method comprising the step of locally administering from about 1 unit to about 2,500 units of a botulinum neurotoxin type A to the penis of the patient, thereby treating premature ejaculation of the patient.

2. The method of claim 1, wherein the administering of the botulinum neurotoxin type A is accomplished by transdermal, intramuscular, subcutaneous, subdermal, intradermal or implant administration.

3. The method of claim 1, wherein the administering of the botulinum neurotoxin type A is by injection.

4. The method of claim 1, wherein the amount of botulinum neurotoxin type A administered is between about 1 units and about 500 units.

5. The method of claim 1, wherein the amount of botulinum neurotoxin type A administered is between about 25 units and about 100 units.

6. The method of claim 1, wherein the amount of botulinum neurotoxin type A administered is between 10 units and about 75 units.

7. A method for treating premature ejaculation in a patient in need thereof, the method comprising the step of locally administering from about 1 unit to about 500 units of a botulinum neurotoxin type A to the penis of the patient, thereby treating premature ejaculation of the patient.

8. The method of claim 7, wherein the administering of the botulinum toxin type A is per patient visit.

9. The method of claim 7, wherein the administering of the botulinum toxin type A is distributed in multiple dosages.

10. The method of claim 9, wherein a first dosage of the botulinum neurotoxin type A administered is from about 10 units to about 75 units.

11. The method of claim 9, wherein a first dosage of the botulinum neurotoxin type A administered is from about 25 units to about 50 units.

12. The method of claim 10, wherein a second dosage of the botulinum neurotoxin type A administered after the first dosage is about 100 units.

13. The method of claim 11, wherein a second dosage of the botulinum neurotoxin type A administered after the first dosage is about 100 units.

14. The method of claim 12, wherein a time interval between the first dosage and the second dosage ranges from about 3 weeks to about 2 months.

15. The method of claim 13, wherein a time interval between the first dosage and the second dosage ranges from about 3 weeks to about 2 months.

16. The method of claim 7, wherein the administering of the botulinum neurotoxin type A is accomplished by transdermal, intramuscular, subcutaneous, subdermal, intradermal or implant administration.

17. The method of claim 7, wherein the administering of the botulinum neurotoxin type A is by injection.

18. The method of claim 7, wherein the administering of the botulinum neurotoxin type A is per injection site.

19. A method for treating premature ejaculation of a patient in need thereof, the method comprising the step of locally administering a botulinum neurotoxin to the penis of the patient, thereby treating premature ejaculation of the patient.

20. The method of claim 19, wherein the botulinum neurotoxin is selected from the group consisting of botulinum toxin types A and B.

* * * * *